US012290668B2

(12) United States Patent
Bendek

(10) Patent No.: US 12,290,668 B2
(45) Date of Patent: *May 6, 2025

(54) CAP ASSEMBLY FOR A MEDICAMENT DELIVERY DEVICE

(71) Applicant: SHL Medical AG, Zug (CH)

(72) Inventor: Antonio Bendek, Wellington, FL (US)

(73) Assignee: SHL Medical AG, Zug (CH)

( * ) Notice: Subject to any disclaimer, the term of this patent is extended or adjusted under 35 U.S.C. 154(b) by 572 days.

This patent is subject to a terminal disclaimer.

(21) Appl. No.: 17/467,563

(22) Filed: Sep. 7, 2021

(65) Prior Publication Data

US 2021/0393887 A1 Dec. 23, 2021

Related U.S. Application Data

(60) Continuation of application No. 16/351,455, filed on Mar. 12, 2019, now Pat. No. 11,141,543, which is a
(Continued)

(51) Int. Cl.
*A61M 5/32* (2006.01)
*A61F 9/00* (2006.01)
(Continued)

(52) U.S. Cl.
CPC ......... *A61M 5/3204* (2013.01); *A61F 9/0008* (2013.01); *A61M 5/3202* (2013.01);
(Continued)

(58) Field of Classification Search
CPC .............. A61M 5/3202; A61M 5/3204; A61M 5/3243; A61M 5/3137; A61M 5/3134; A61M 5/31511; A61M 2005/3139
See application file for complete search history.

(56) References Cited

U.S. PATENT DOCUMENTS 9,757,521 B2 * 9/2017 McLoughlin ....... A61M 5/3213
2009/0182284 A1 * 7/2009 Morgan ............. A61M 5/3202
604/227
(Continued)

FOREIGN PATENT DOCUMENTS

CN 101945679 A 1/2011
EP 3574942 A1 12/2019
(Continued)

OTHER PUBLICATIONS

European Examination Report for European Application No. 17173203.5 dated Apr. 21, 2021.
(Continued)

*Primary Examiner* — Michael J Tsai
*Assistant Examiner* — Justin L Zamory
(74) *Attorney, Agent, or Firm* — McDonnell Boehnen Hulbert & Berghoff LLP

(57) ABSTRACT

This disclosure relates to a cap assembly for a medicament delivery device that has a cap body arranged to be connected to a medicament delivery device for protecting and for removing a medicament delivery member shield. The cap body has an inner cap structure defining a channel extending along the central axis of the cap body, and a gripping member configured to be received in the channel with a friction fit and to receive a medicament delivery member shield. The gripping member has a first leg, a second leg, and a transverse portion extending between the first leg and the second leg, which transverse portion defines the leading edge of the gripping member when received by the channel.

16 Claims, 5 Drawing Sheets

Related U.S. Application Data division of application No. 15/180,424, filed on Jun. 13, 2016, now Pat. No. 10,335,553.

(51) Int. Cl.
*A61M 15/00* (2006.01)
*A61M 5/20* (2006.01)

(52) U.S. Cl.
CPC ........... *A61M 15/0001* (2014.02); *A61M 5/20* (2013.01); *A61M 5/3243* (2013.01); *A61M 2207/00* (2013.01)

(56) References Cited

U.S. PATENT DOCUMENTS

2010/0016795 A1 1/2010 McLoughlin
2014/0358072 A1 12/2014 McLoughlin

FOREIGN PATENT DOCUMENTS

| IN | 104394910 A | 3/2015 |
| TW | 201004665 A | 2/2010 |
| TW | 201315504 A | 4/2013 |
| WO | 2009081103 A1 | 7/2009 |
| WO | 2009081130 A1 | 7/2009 |
| WO | 2010089589 A1 | 8/2010 |
| WO | 2015110532 A1 | 7/2015 |

OTHER PUBLICATIONS

European Examination Report for European Application No. 17173203.5 dated Nov. 10, 2017.
Office Action for Chinese Application No. 20170441997.8, issued Dec. 21, 2020.

* cited by examiner

CAP ASSEMBLY FOR A MEDICAMENT DELIVERY DEVICE

CROSS REFERENCE TO RELATED APPLICATIONS

The present application is a continuation of U.S. patent application Ser. No. 16/351,455 filed Mar. 12, 2019, which is divisional of U.S. patent application Ser. No. 15/180,424 filed Jun. 13, 2016, the contents of both of which are hereby incorporated by reference into the present application.

TECHNICAL FIELD

The present disclosure generally relates to medical devices. In particular, it relates to a cap assembly for a medicament delivery device, to a medicament delivery device comprising the same, and to a method of assembling a medicament delivery device.

BACKGROUND

Medicament delivery devices, such as injectors and inhalers, typically comprise a housing in which a medicament container containing a medicament is to be arranged. Upon activation of the medicament delivery device, the medicament is expelled through a medicament delivery member, for example a needle or a nozzle.

In order to protect and to keep the medicament delivery member sterile, the medicament delivery member may be provided with a medicament delivery member shield, or sheath, such as a Flexible Needle Shield (FNS) or a Rigid Needle Shield (RNS). The medicament delivery member shield may thus be attached to the medicament container to cover the medicament delivery member, during assembly of the medicament container or of the medicament delivery device.

Moreover, the medicament delivery device may comprise a removable cap which is mounted to the proximal end of the housing, i.e. that end which is placed towards the injection site during medicament delivery, of the medicament delivery device, or to the proximal end of the medicament container. The removable cap has the function of providing mechanical protection of the medicament delivery member while attached to the housing or medicament container, and to remove the medicament delivery member shield when the cap is removed from the housing.

WO2015/110532 A1 discloses an auto-injector having a connector for connecting a needle cover to a removable cap. The connector has a plurality of legs spaced symmetrically away from one another about a central hub. The legs have an elastic nature and aid in securing the needle cover and/or rigid needle shield to a cap insert and hence to the removable cap. The needle cover and/or needle shield are secured together through upper, internally facing barbs protruding from the first legs. The upper, internally facing barbs include tips that point toward the forward end of the connector. These barbs are shaped to engage the needle cover and/or rigid needle shield when the needle cover and/or rigid needle shield is fitted within the connector. The barb tips apply opposing force with respect to one another when the engage the needle cover and/or rigid needle shield when the needle cover and/or rigid needle shield is fitted within the connector.

SUMMARY

According to the design disclosed in WO2015/110532 A1, the legs of the connector are flexed towards each other as soon as the connector is placed in the cap insert. This bending of the legs renders it more difficult to insert the needle cover/rigid needle shield into the connector, thereby making assembly more difficult.

In view of the above, a general object of the present disclosure is to provide a cap assembly which simplifies assembly of a medicament delivery device.

There is hence according to a first aspect of the present disclosure provided a cap assembly for a medicament delivery device, the cap assembly comprising: a cap body arranged to be connected to a medicament delivery device for protecting and for removing a medicament delivery member shield, which cap body has an inner cap structure defining a channel extending along the central axis of the cap body, and a gripping member configured to be received in the channel with a friction fit and to receive a medicament delivery member shield, wherein the gripping member has a first leg, a second leg, and an transverse portion extending between the first leg and the second leg, which transverse portion defines the leading edge of the gripping member when received by the channel, each of the first leg and the second leg having a respective proximal portion extending distally from the transverse portion and extending parallel to each other, the first leg and the second leg also having a respective distal portion, the distal portions being radially flexible and extending away from each other to allow the gripping member to receive a medicament delivery member shield between the distal portions, each distal portion being provided with a medicament delivery member shield gripper configured to engage with a medicament delivery member shield when the gripping member is pushed into the channel and the distal portions flex radially inwards.

Each medicament delivery member shield gripper is hence configured to engage with the medicament delivery member shield when the gripping member is pushed into the channel by the medicament delivery member shield, causing the distal portions to flex radially inwards.

Due to the design of the gripping member, in particular the first leg and the second leg where the proximal portions extend parallel and the distal portions are inclined and radially extend outwards, in the distal direction, the gripping member will not flex radially inwards initially when received by the channel of the inner cap structure. The gripping member will only flex radially inwards once the proximal portions have been fully received and the distal portions are being received. This facilitates assembly when the medicament delivery member shield is initially to be received by the gripping member, as the distal portions, with their medicament delivery member grippers, will still be in their initial outwards extending position until also the distal portions are received by the channel. Tolerances for assembly are tight, and thus the proposed design may facilitate the assembly procedure.

According to one embodiment each medicament delivery member shield gripper extends radially inwards.

According to one embodiment each medicament delivery member shield gripper is formed by a radially inwardly curved end portion of the corresponding distal portion.

According to one embodiment each distal portion has a straight extension from the corresponding proximal portion to the medicament delivery member shield gripper.

According to one embodiment each proximal portion has a straight extension from the transverse portion to the corresponding distal portion.

According to one embodiment the channel has opposing inner walls that extend parallel in the longitudinal direction.

According to one embodiment the opposing inner walls extend parallel with each other along the entire extension of the channel.

According to one embodiment the gripping member is made of metal. The gripping member could alternatively be made of for example plastic.

According to one embodiment the gripping member is configured to engage with an inner wall of the channel when the gripping member is maximally received in the channel, thereby locking the gripping member in a maximally received position.

According to one embodiment the gripping member and an inner wall of the channel are configured to engage to retain the gripping member in the inner cap structure.

According to one embodiment the inner cap structure has radial through-openings, and each of the first leg and the second leg of the gripping member has a flexible portion arranged between the proximal portion and the distal portion, which flexible portion in a first state has a radially outwards extending curvature, wherein the radial through-openings are configured to receive a respective flexible portion when the gripping member is received by the channel.

According to one embodiment each distal portion is provided with a radially outwards extending protrusion configured to engage with a distal end of the inner cap structure to thereby prevent the distal portions from being received in the channel.

According to one embodiment the flexible portions are configured to straighten out when the transverse portion is pushed proximally in the channel and the radially outwards extending protrusions engage with the distal end of the inner cap structure, to obtain a second state, the flexible portions thereby extending parallel with each other when the gripping member is maximally received in the channel.

According to one embodiment the flexible portions are bi-stable with respect to the first state and the second state.

According to a second aspect of the present disclosure there is provided a medicament delivery device comprising: a housing arranged to receive a medicament container and a medicament delivery member shield, which housing has a proximal end and a distal end, and a cap assembly according to the first aspect, configured to be mounted adjacent to the proximal end of the housing.

One embodiment comprises a medicament delivery member shield, wherein the longitudinal extension of the first leg and the second leg is longer than the length of the medicament delivery member shield to allow the medicament delivery member shield grippers to engage with a distal end of the medicament delivery member shield when the medicament delivery member shield and the distal portions are arranged in the channel of the inner cap structure.

One embodiment comprises a medicament delivery member shield that has a flexible rubbery external surface, wherein the longitudinal extension of the first leg and the second leg is shorter than the length of the medicament delivery member shield to allow the medicament delivery member shield grippers to engage with the external surface of the medicament delivery member shield when the medicament delivery member shield and the distal portions are arranged in the channel of the inner cap structure.

According to one embodiment the medicament delivery device is one of an injector, an inhaler and an eye dispenser.

According to a third aspect, there is provided a method of assembling a medicament delivery device, comprising: a) providing a cap assembly comprising: a cap body having an inner cap structure defining a channel extending along the central axis of the cap body and configured to receive a medicament delivery member shield, and a gripping member configured to be received in the channel with a friction fit and to receive a medicament delivery member shield, wherein the gripping member has a first leg, a second leg, and an transverse portion extending between the first leg and the second leg, each of the first leg and the second leg having a respective proximal portion extending distally from the transverse portion and extending parallel to each other, the first leg and the second leg also having a respective distal portion, the distal portions being radially flexible and extending away from each other to allow the gripping member to receive a medicament delivery member shield between the distal portions, each distal portion being provided with a medicament delivery member shield gripper, b) pushing the gripping member partly into the channel, with the transverse portion defining the leading edge of the gripping member so that the distal portions extend distally from the channel, c) placing the cap assembly at a proximal end of the medicament delivery device, d) placing a medicament container assembly including a medicament delivery member shield into the housing, from a distal end of the housing, e) moving the medicament container assembly in a proximal direction inside the housing until the medicament delivery member shield is received between the first leg and the second leg, and the gripping member is pushed proximally by the medicament delivery member shield to such an extent that the distal portions are pushed radially inwards by inner walls of the channel and the medicament delivery member shield grippers engage with the medicament delivery member shield.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE FIGURES

The specific embodiments of the inventive concept will now be described, by way of example, with reference to the accompanying drawings, in which.

DETAILED DESCRIPTION

Figure 1:
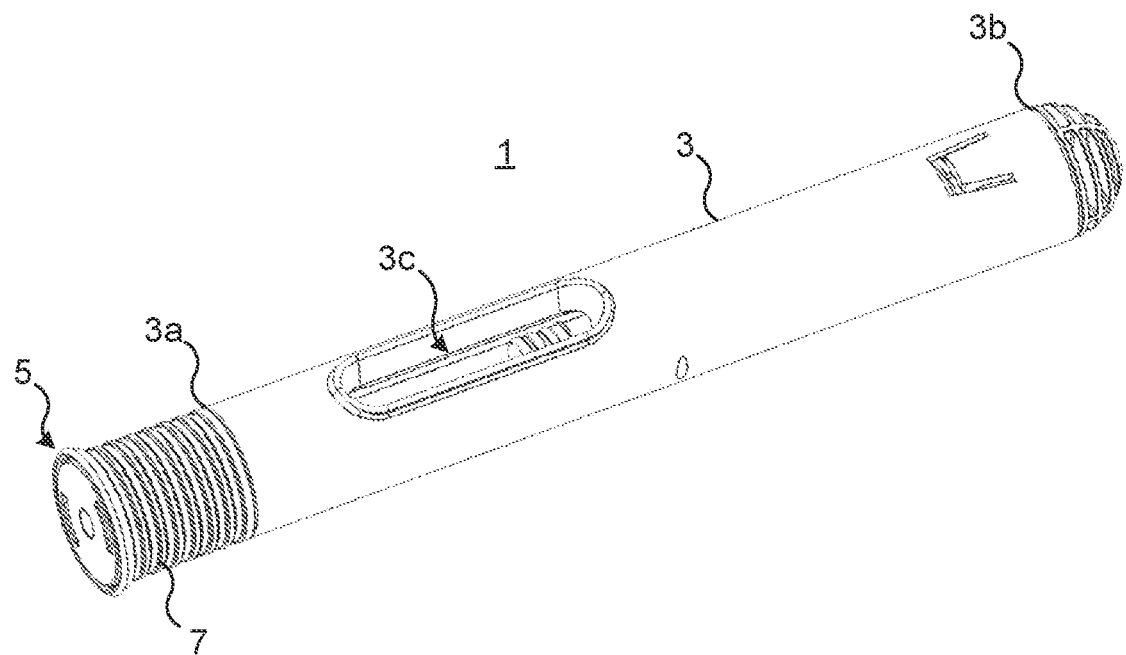
FIG. 1 is a perspective view of an example of a partly assembled medicament delivery device.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with a cap assembly, refers to that end of the cap assembly which, when mounted to a medicament delivery member shield installed on a medicament delivery member in a medicament delivery device, forms the proximal end face of the medicament delivery device. The proximal end of the medicament delivery device is hence that end which is to be pointed towards the site of injection during medicament expulsion. The same considerations also apply when referring to any component of the cap assembly, i.e. the cap body and the gripping member. The "distal end" is the opposite end relative to the proximal end. With "proximal direction" and, equivalently, "proximally" is meant a direction from the distal end towards the proximal end, along the central axis of the cap assembly. With "distal direction" or "distally" is meant the opposite direction to "proximal direction".

The present disclosure relates to a cap assembly for a medicament delivery device. The cap assembly is configured to be mounted to a medicament delivery member shield thereby protecting the medicament delivery member shield and the medicament delivery member. The cap assembly is furthermore configured to engage with the medicament delivery member shield such that removal of the cap assembly from the medicament delivery device removes the medicament delivery member shield from the medicament container prior to medicament administration. The medicament delivery member shield may be made of a rigid material or a flexible/rubbery material. To this end, the medicament delivery member shield may for example be a rigid needle shield or a flexible needle shield.

The cap assembly includes a cap body which when mounted to a medicament delivery member shield installed in a medicament delivery device forms part of a housing assembly enclosing the internal components of the medicament delivery device. Such internal components include the medicament delivery member and a medicament container. To this end, the cap assembly has an external surface forming part of the housing assembly, and an internal structure including an inner cap structure defining a channel extending coaxially with the central longitudinal axis of the cap body. The central longitudinal axis of the cap body coincides with the central longitudinal axis of the housing when the cap body is fitted to the medicament delivery device. The inner cap structure is configured to receive a medicament delivery member shield.

Moreover, the cap assembly includes a longitudinal gripping member configured to receive a medicament delivery member shield and to be received in the channel of the inner cap structure with a friction fit. The longitudinal gripping member has a first leg and a second leg, and a transverse portion or connecting portion, which extends between the first leg and the second leg. The transverse portion may be seen as a hub portion.

The first leg and the second leg are arranged opposite to each other and extend longitudinally from the transverse portion in a distal direction, generally parallel with a central axis of the gripping member. Each first leg has a proximal portion essentially parallel with the central axis and a distal portion. The distance between the outer surfaces of the two proximal portions essentially corresponds to the distance between opposing inner surfaces of the channel, whereby the proximal portions are configured to be received with a friction fit in the channel.

The distal portions of the first leg and the second leg are radially flexible and extend away from each other in a distal direction. The distal portions thereby form a distal mouth of the gripping member.

Each of the two distal portions has a medicament delivery device shield gripper configured to engage with a medicament delivery member shield when the gripping member is received in the channel and the distal portions have been bent radially inwards by the inner walls of the channel, so that they extend essentially parallel with the central axis of the gripping member.

Examples of cap assemblies and a medicament delivery device comprising a cap assembly will now be described with reference to FIGS. 1-5c.

FIG. 1 shows an example of a medicament delivery device 1, which has not been fully assembled. In particular, the exemplified medicament delivery device 1 has an end cap or end portion which has not yet been mounted.

Medicament delivery device 1 has a housing 3 having a proximal end 3a and a distal end 3b. The housing 3 is furthermore provided with an inspection window 3c enabling a user to inspect medicament contained in a medicament container installed in the medicament delivery device 1.

Medicament delivery device 1 also has a cap assembly 5 including a cap body 7 and a gripping member, not shown in FIG. 1. The cap assembly 5 is configured to be mounted to a medicament delivery member shield arranged inside the housing 3. The cap assembly is thus designed to form a proximal end part of the medicament delivery device 1.

Figure 2:
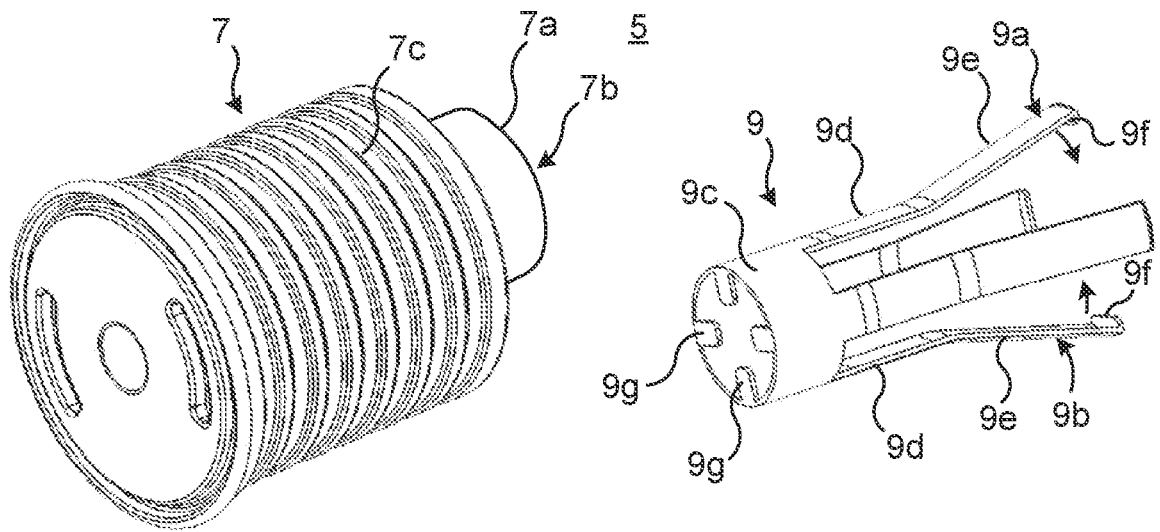
FIG. 2 is a perspective view of an example of a cap assembly for the medicament delivery device in FIG. 1.

Turning now to FIG. 2, a perspective view of the cap assembly 5 is here shown. As mentioned above, the cap assembly includes the cap body 7 and the gripping member 9, of which a first example is depicted. The exemplified cap body 7 has an inner and an outer concentrically arranged cylinder structure. To this end, the cap body 7 has an external surface 7c having an essentially cylindrical structure and an inner cap structure 7a which also is essentially cylindrical. The inner cap structure 7a is hollow and defines a longitudinal channel 7b that has a distal end opening. The channel 7b is configured to slidably and with a friction fit, receive the gripping member 9 during assembly of the medicament delivery device 1.

The gripping member 9 has a longitudinal body provided with a first leg 9a, a second leg 9b, and a transverse portion, or connecting portion, 9c. The transverse portion 9c connects the first leg 9a and the second leg 9b. The transverse portion 9c may for example be essentially cylindrical or cylindrical. The first leg 9a and the second leg 9b extend from the transverse portion 9c at about 180 degrees angle relative to each other, as seen in the circumferential direction. The first leg 9a and the second leg 9b are hence arranged opposite to each other.

Each of the first leg 9a and the second leg 9b has a respective proximal portion 9d extending longitudinally in the distal direction from the transverse portion 9c. The proximal portions 9d are parallel or essentially parallel with each other and thus parallel with the central axis of the gripping member 9. Each of the first leg 9a and the second leg 9b also has a respective distal portion 9e. Each distal portion 9e extends from a respective proximal portion 9d. The distal portions 9e extend radially outwards, in the distal direction. The radial distance between the oppositely arranged distal portions 9e hence increases in the distal direction. The distal portions 9e form a distal mouth of the gripping member 9, allowing the gripping member 9 to receive a medicament delivery member shield between the first leg 9a and the second leg 9b.

Each distal portion 9e is provided with a respective medicament delivery member shield gripper 9f According to the present example, the distal end of each distal portion 9e is provided with the medicament delivery member shield grippers 9f In the present variation, the medicament delivery member shield grippers 9f extend radially inwards. In the exemplified gripping member 9, the distal portions 9e extending between the proximal ends 9d and the medicament delivery member shield grippers 9f are inclined with respect to the central axis of the gripping member 9, and essentially straight, i.e. non-curved.

The distal portions 9e are radially flexible or elastic, so that when sufficiently large radial inward-pointing forces are applied to the distal portions 9e during assembly of the medicament delivery device 1, the distal portions 9e will be bent radially inwards, as indicated by the arrows in FIG. 2, so that the medicament delivery member shield grippers 9f are moved towards each other until the distal portions 9e are essentially parallel. The medicament delivery member shield grippers 9f may thereby engage with a medicament delivery member shield.

The gripping member 9 may for example be made of metal, such as steel or aluminium, or a plastic material.

In FIG. 2 the gripping member 9 is shown in a state prior to assembly with the cap body 7, with the distal portions 9e of the first leg 9a and the second leg 9b extending radially outwards in the distal direction along a central axis of the gripping member 9.

The exemplified gripping member 9 has four legs for reasons of symmetry. Alternatively, the gripping member could be provided with only two legs arranged oppositely relative to each other. There could also be more than four legs, in theory generally any integer number that is evenly divisible with the integer two for symmetry, or even odd number of legs if the legs are evenly spaced in the circumferential direction. The transverse portion 9c may optionally also be provided with radial support structures 9g, as shown in FIG. 2. The radial support structures 9g extend radially inwards towards the central axis of the gripping member 9. The radial support structures 9g are configured to prevent a medicament delivery member shield from sliding past the proximal end of the gripping member 9, in the proximal direction, when pushed into the gripping member 9 and the channel 7b of the cap body 7. The medicament delivery member shield will thereby move the gripping member 9 proximally during assembly, once the medicament delivery member shield reaches the radial support structures 9g.

Figure 3:
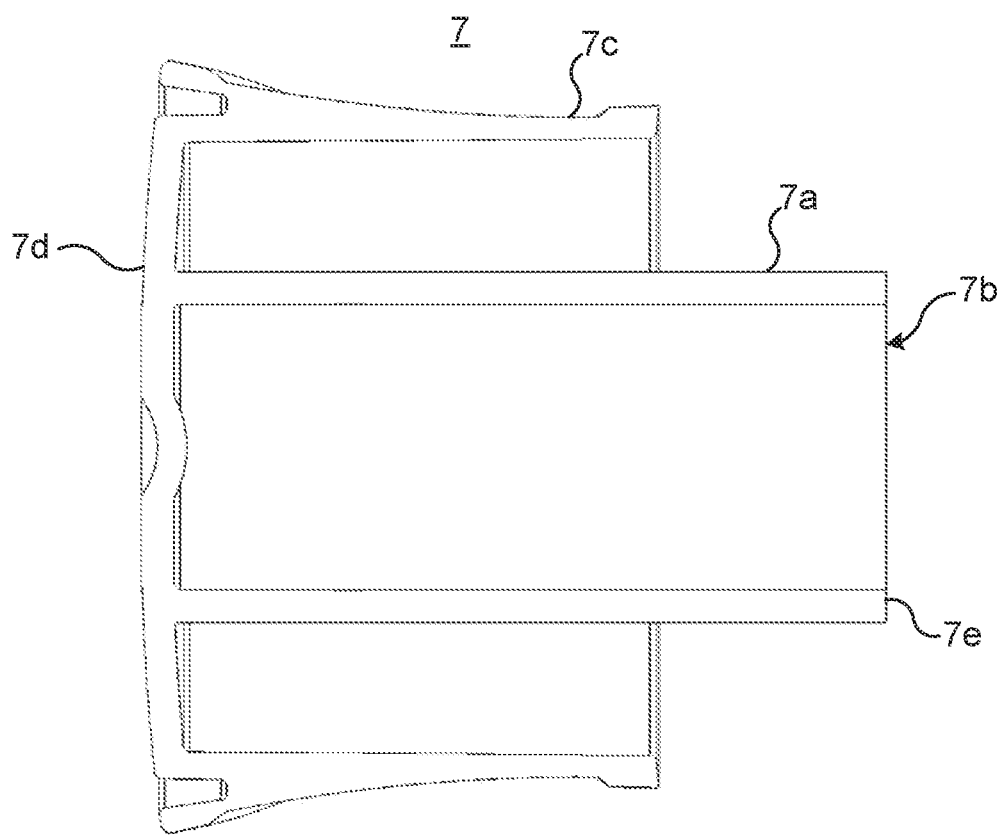
FIG. 3 is a longitudinal section of the cap body in FIG. 2.

FIG. 3 shows a longitudinal sectional view of the cap body 7, along the central longitudinal axis thereof. According to the example in FIG. 3, cap body 9 has an external surface 7c which forms part of the external surface of the housing assembly that also includes the housing 3, of the medicament delivery device 1, for protecting internal components thereof. As previously mentioned, the inner cap structure 7b is coaxial with and concentrically arranged with the external surface 7c of the cap body 7. The inner cap structure 7b forms an essentially cylindrical channel 7b having a distal end opening for receiving the gripping member 9 and a medicament delivery member shield having been received between the first leg 9a and the second leg 9b of the gripping member 9. It is the engagement between the gripping member 9 and the medicament delivery member shield that retain the cap body 7 in a mounted state in which it forms part of the housing assembly.

The cap body 7 has a proximal end 7d with a radial surface which according to the present example is closed in the sense that in a mounted state it forms a closed front wall of the medicament delivery device 1. The cap body 7 also has a distal end 7e which according to the example is formed by the distal end of the inner cap structure 7b. According to the example, the longitudinal extension of the inner cap structure 7b is greater than the longitudinal extension of the external surface 7c of the cap structure 7. The cap body 7 may thereby receive a greater portion of a medicament delivery member shield, for a more secure fit or engagement therewith.

Figure 4A:
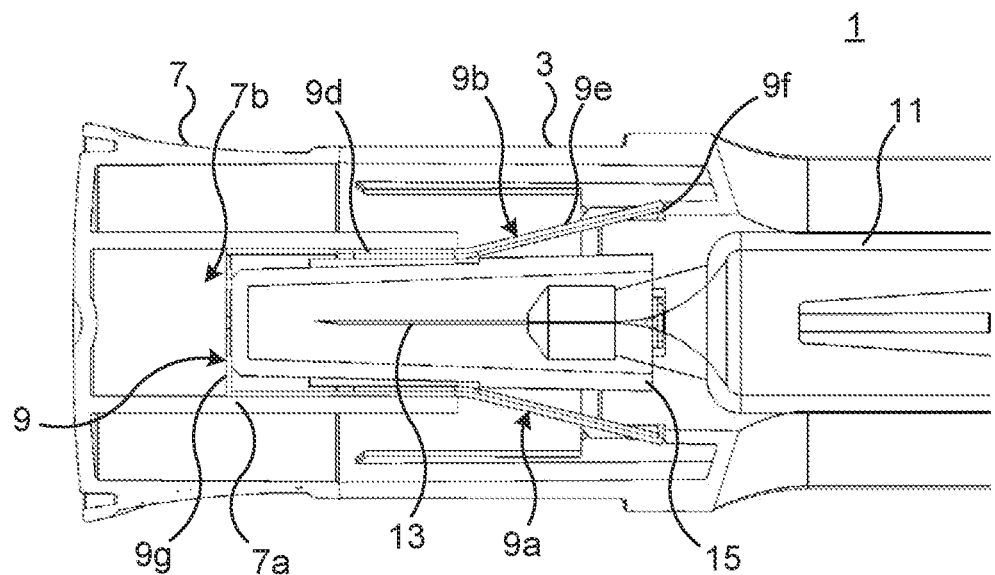
FIG. 4a shows a longitudinal section of a proximal portion of the medicament delivery device in FIG. 1 before the cap assembly has been fully assembled with a medicament delivery member shield.
Figure 4B:
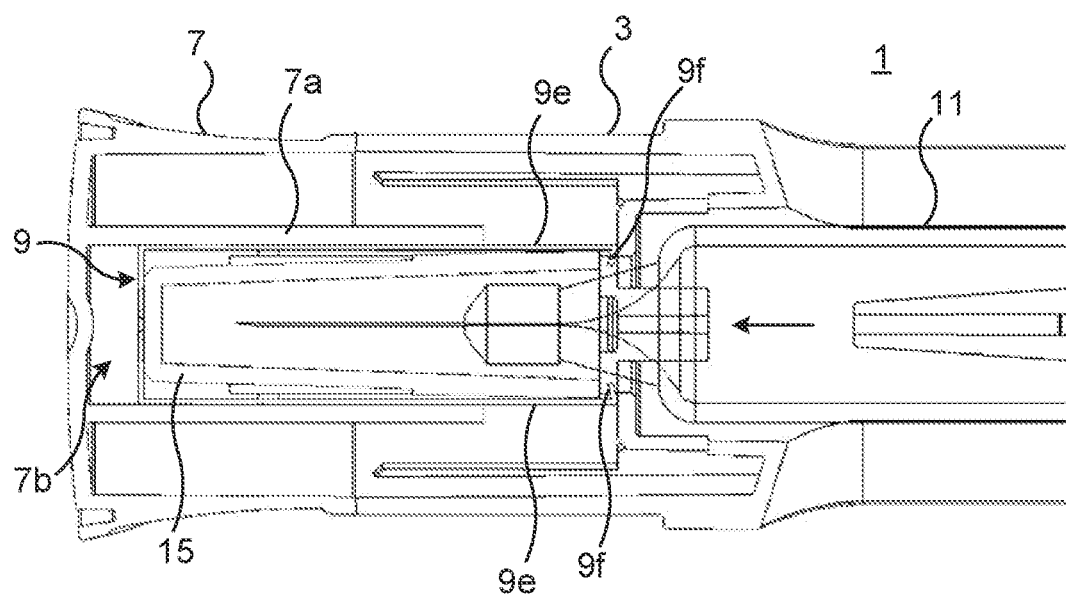
FIG. 4b is a longitudinal section of a proximal portion of the medicament delivery device in FIG. 1 when the cap assembly has been assembled with the medicament delivery member shield.
Figure 4C:
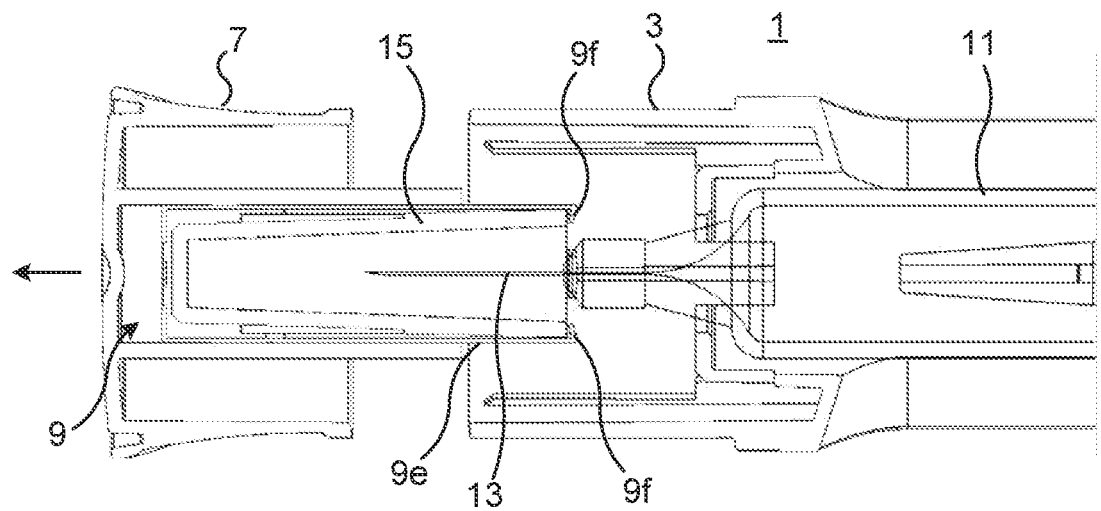
FIG. 4c is a longitudinal section of a proximal portion of the medicament delivery device in FIG. 1 when the cap body has been pulled from the housing of the medicament delivery device to expose a medicament delivery member.

With reference to FIGS. 4a-4c the operation of the cap assembly 5 will now be shown during assembly of a medicament delivery device 1 and when preparing the medicament delivery device 1 for medicament administration.

During assembly, the gripping member 9 is arranged in channel 7b of the inner cap structure 7a, with the transverse portion 9c forming the leading edge of the gripping member 9 when being placed in the channel 7b. The gripping member 9 is at this stage not yet received in its final position in the channel 7b. The gripping member 9 is hence movable proximally in the channel 7b during the forthcoming assembly stage.

In FIG. 4a a medicament container 11 has been mounted into the housing 3 of the medicament delivery device 1. The medicament container 11 is advantageously inserted from a distal end opening in the housing 3 in this stage and moved proximally within the housing 3. The above-described step of assembly of the cap assembly 5 has advantageously already been performed at this stage.

According to the example in FIG. 4a, the medicament delivery device 1 is an injector, and the medicament delivery member is a needle 13. In FIG. 4a a medicament delivery member shield 15 has been mounted onto the medicament container 11, thus protecting the needle 13. The cap body 7 is furthermore in position and forms a continuation of the housing 3, thereby protecting internal components of the medicament delivery device 1.

The medicament delivery member shield 15 has not yet been fully received by the inner cap structure 7a into the channel 7b. It has however been received fully between the first leg 9a and the second leg 9b of the gripping member 9. The proximal end of the medicament delivery member shield 15 bears against the radial support structures 9g of the gripping member 9. The distal portions 9e of the first leg 9a and the second leg 9b extend radially outwards in the distal direction, which is the default state of the gripping member 9.

In FIG. 4b, the medicament delivery member shield 15 and the gripping member 9 have been maximally received into the channel 7b of the inner cap structure 7a. With "maximally received" is here meant that the medicament delivery member shield 15 and the gripping member 9 have been received into a final assembly position in the channel 7b. This position is achieved by moving the medicament container 11 further in the proximal direction within the housing 3, as illustrated by the arrow. The proximal end of the medicament delivery member shield 15 thereby pushes the radial support structures 9g, and thus the gripping member 9, in the proximal direction further into the channel 7b. The distal portions 9e of the first leg 9a and the second leg 9b will thereby be received in the channel 7b. The distal portions 9e will thus bear against the inner walls of the channel 7b, and as a result be bent radially inwards to extend essentially parallel with the inner walls of the channel 7b. The medicament delivery member shield grippers 9f will therefore move radially inwards to engage with the medicament delivery member shield 15. As per the present example, the axial length of the gripping member 9 is greater than that of the medicament delivery member shield 15, which is thereby fully received by the gripping member 9. The medicament delivery member shield grippers 9f extend beyond the distal edge of the medicament delivery member shield 15. Moreover, the medicament delivery member shield grippers 9f extend radially inwards beyond the outer diameter of the medicament delivery member shield 15 so that the medicament delivery member shield grippers 9f can engage with the distal edge or distal end of the medicament delivery member shield 15 when the cap body 7 is pulled off, i.e. removed. It should however be noted, that as an alternative to the illustrated example, the medicament delivery member grippers could be configured to grip into the external surface of the medicament delivery member shield in case the medicament delivery member shield 15 is made of a rubbery or flexible material, and the gripping member is made shorter longitudinally than the longitudinal extension of the medicament delivery member shield.

There are a plurality of possible solutions for the gripping member 9 to maintain engagement with the inner wall of the channel 7b, so that the gripping member 9 is retained or locked in a fixed position when the cap body 7 is pulled off the medicament delivery device 1. The gripping member 9 may for example be attached to the inner wall of the channel 7b by means of an adhesive such as glue, or it may be fastened by designing the size and external surface structure of the gripping member to maintain its position by friction, or the gripping member may be configured to engage with the inner wall of the channel 7b when the gripping member reaches its final position. To this end, the inner wall of the channel 7b may be provided with a radial recess and the outer surface of the gripping member may be provided with a corresponding radial protrusion. Alternatively, the inner wall may be provided with a radial protrusion and the outer surface of the gripping member may be provided with a corresponding radial recess for engagement there between.

FIG. 4c shows a situation in which the cap body 7 is being pulled off the medicament delivery device 1, as illustrated by the arrow. As can be seen, the medicament delivery member shield grippers 9f engage with the distal edge of the medicament delivery member shield 15. Due to the fixed position of the gripping member 9 in the channel 7b, the gripping member 9 will pull the medicament delivery member shield off the medicament container 11 to thereby eventually expose the needle 13 when the cap body 7 has been fully removed from the remainder of the medicament delivery device 1.

Figure 5A:
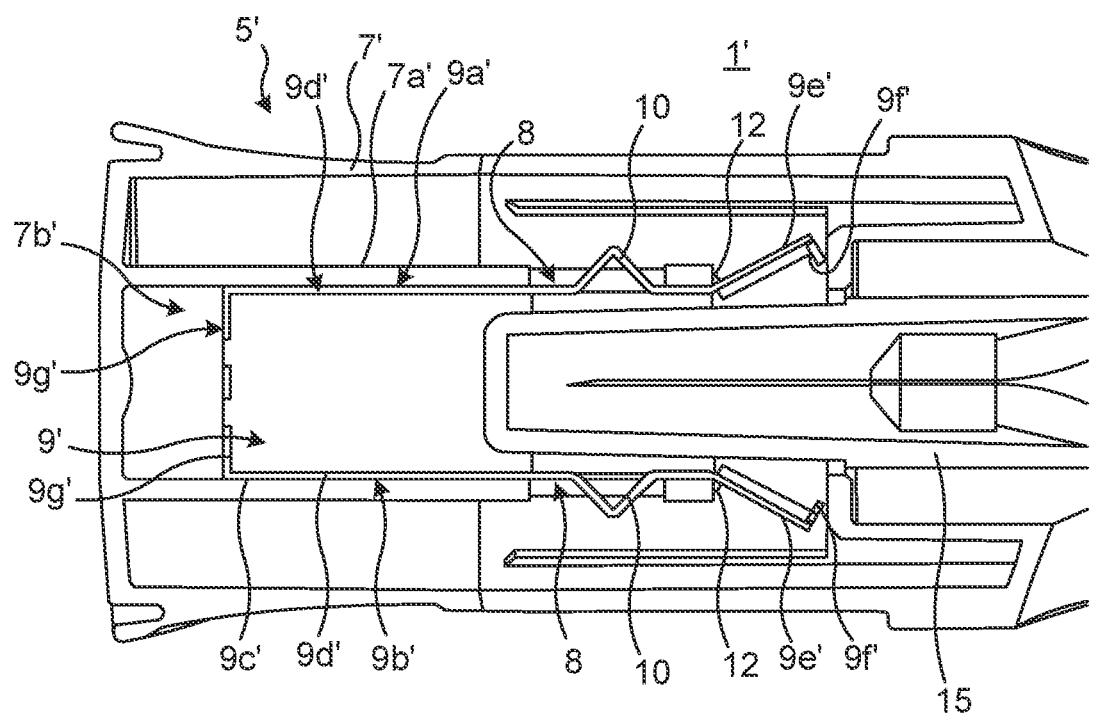
FIGS. 5a-c show longitudinal sections of a medicament delivery device being assembled with another example of a cap assembly.

FIG. 5a shows a medicament delivery device 1' provided with another example of a cap assembly. FIG. 5a shows the medicament delivery device 1' during the assembly stage, when the cap assembly 5' and the medicament delivery device shield 15 have not yet been fully mounted to each other.

Cap assembly 5' has a cap body 7' similar to the previously described cap body 7. To this end, cap body 7' has an inner cap structure 7a', which defines a longitudinal channel 7b' having a distal opening and extending proximally towards the proximal end face of the cap body 7a'. The inner cap structure 7a' has radial through-openings 8 arranged oppositely relative to each other. The radial through-openings 8 are arranged in a distal portion of the inner cap structure 7a'.

In a similar manner as the previous example, gripping member 9' has a transverse portion 9c' and radial support structures 9g', a first leg 9a' and a second leg 9b'. Each of the first leg 9a' and the second leg 9b' has a proximal portion 9d', which proximal portions 9d' extend parallel to each other, and a distal portion 9e'. The distal portions 9e' are provided with medicament delivery member shield grippers 9f' configured to engage with a medicament delivery member shield 15. In their default state, the distal portions 9e' each have a radially outwards extend section in the distal direction, and are radially flexible. According to the present example, each of the first leg 9a' and the second leg 9b' also has a flexible portion 10 extending between the proximal portion 9d' and the distal portion 9e'. The flexible portion 10 is, in a first state, curved radially outwards. The flexible portion 10 hence has a radially outwards extending curvature in the first state. The flexible portion 10 may for example in the first state have a triangular shape in a side view. Each distal portion 9e' furthermore has a radially outwards extending protrusion 12, arranged in the distal direction prior to the radially outwards extending section of the distal portion 9e'.

Figure 5B:
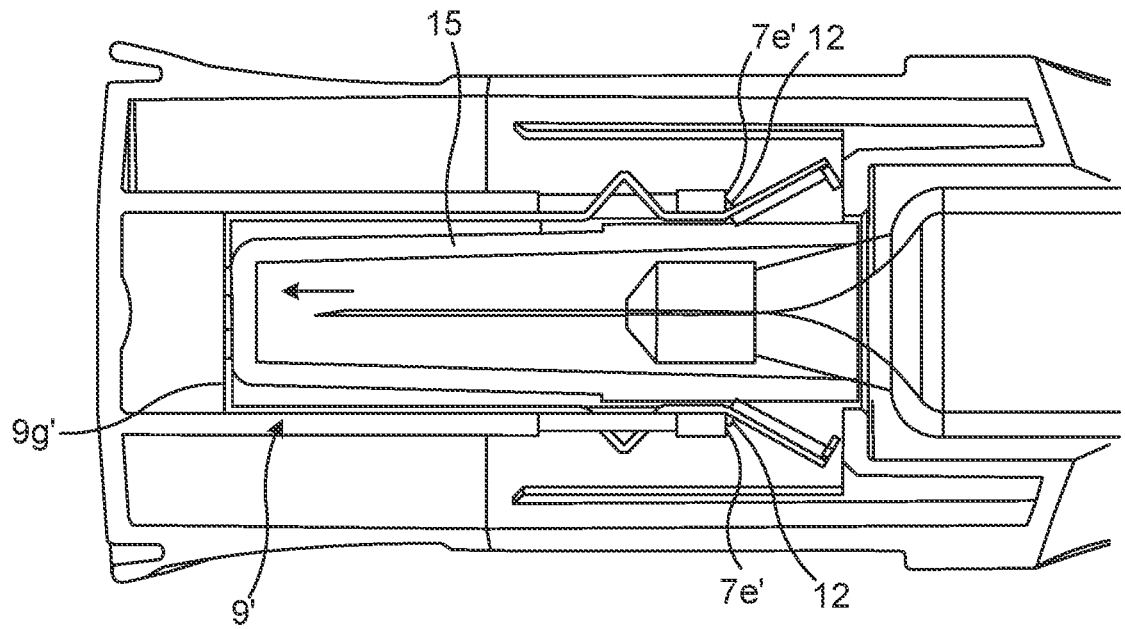

In FIG. 5b, the medicament delivery member shield 15 has been fully inserted into the gripping member 9', bearing against the radial support structures 9g'. In this position, the radially outwards extending protrusions 12 engage with the distal end 7e', a flange surface, of the inner cap structure 7a'. The radially outwards extending section of the distal portions 9e' can therefore not be received by the channel 7b'.

Figure 5C:
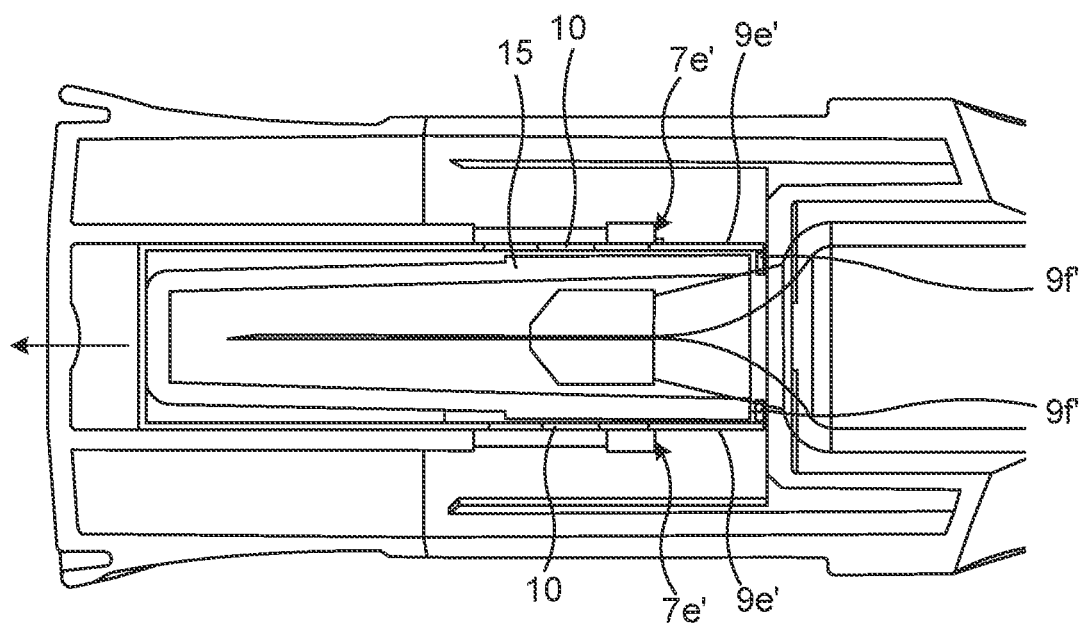

In FIG. 5c, the medicament delivery member shield 15 has brought forward the gripping member 9' by straightening out the flexible portion 10, compared to the state shown in FIG. 5b, thereby obtaining a second state. The radially outwards extending protrusions 12 act as a fulcrum when the flexible portions 10 are straightened out, about which the radially outwards extending sections of the distal portions 9e' can pivot. The distal portions 9e' are therefore flexed or pivoted radially inwards, and the medicament delivery member shield grippers 9f' engage with the distal end or edge of the medicament delivery member shield 15. The flexible portion 10 may thus have a bi-stable functionality or structure.

Each flexible portion 10 may for example have three transverse cuts to form a triangular-shaped curve in the first state, to facilitate flexing from the first state to the second state.

The medicament delivery device utilising the cap assembly according to the present invention may for example be a manual injector, an auto-injector, an inhaler, or an eye dispenser.

The inventive concept has mainly been described above with reference to a few examples. However, as is readily appreciated by a person skilled in the art, other embodiments than the ones disclosed above are equally possible within the scope of the inventive concept, as defined by the appended claims.

I claim:

1. A gripping member for a cap assembly of a medicament delivery device, the gripping member comprising:
   a first leg extending distally from a proximal end of the gripping member, wherein the first leg includes a first proximal portion and a first distal portion, and wherein the first distal portion of the first leg includes a first medicament delivery member shield gripper that extends radially inward from the first distal portion of the first leg; and a second leg extending distally from the proximal end of the gripping member, wherein the second leg includes a second proximal portion and a second distal portion, wherein the second distal portion of the second leg includes a second medicament delivery member shield gripper that extends radially inward from the second distal portion of the second leg, and wherein a distance between the first proximal portion of the first leg and the second proximal portion of the second leg is greater than a distance between the first distal portion of the first leg and the second distal portion of the second leg when the first leg and the second leg are in a first position, wherein when the first flexible portion and the second flexible portion are in a first state the first flexible portion and the second flexible portion each have a radially outwards extending curvature, and wherein the first flexible portion and the second flexible portion each have a triangular shape in a side view in the first state.

2. The gripping member of claim 1, further comprising:
a transverse portion positioned at the proximal end of the gripping member, wherein the transverse portion extends between the first leg and the second leg.

3. The gripping member of claim 2, wherein the transverse portion is cylindrical.

4. The gripping member of claim 1, wherein the first proximal portion and the second proximal portion are generally parallel to each other.

5. The gripping member of claim 1, wherein the first distal portion of the first leg and the second distal portion of the second leg are configured to transition from the first position to a second position, wherein when in the first position the first distal portion of the first leg and the second distal portion are not parallel to each other, and wherein when in the second position the first distal portion of the first leg and the second distal portion are generally parallel to each other.

6. The gripping member of claim 5, wherein the distance between the first proximal portion of the first leg and the second proximal portion of the second leg is equal to the distance between the first distal portion of the first leg and the second distal portion of the second leg when the first leg and the second leg are in the second position.

7. The gripping member of claim 5, wherein the first medicament delivery member shield gripper and the second medicament delivery member shield gripper are each shaped to abut and engage a medicament delivery member shield when the first distal portion and the second distal portion are in the second position.

8. The gripping member of claim 1, wherein the first distal portion of the first leg and the second distal portion are radially flexible and extend away from each other to allow the gripping member to receive a medicament delivery member shield between the first distal portion of the first leg and the second distal portion.

9. The gripping member of claim 1, further comprising:
a first flexible portion arranged between the first proximal portion and the first distal portion of the first leg; and a second flexible portion arranged between the second proximal portion and the second distal portion of the second leg.

10. The gripping member of claim 1, wherein when the first flexible portion and the second flexible portion are in a second state the first flexible portion and the second flexible portion are each in a straightened out configuration.

11. The gripping member of claim 1, wherein the proximal end of the gripping member includes one or more radial support structures that extend radially inward towards a central axis of the gripping member.

12. A cap assembly for a medicament delivery device, the cap assembly comprising:
a cap body comprising an inner cap structure having radial through-openings and defining a channel extending along a central axis of the cap body, where the channel has an open end; and the gripping member of claim 1, wherein the gripping member is configured to be received in the channel with a friction fit, wherein the first position of the gripping member corresponds to a first axial position of the gripping member relative to the inner cap structure, and wherein a second position of the gripping member corresponds to a second axial position of the gripping member relative to the inner cap structure.

13. The cap assembly of claim 12, wherein when the gripping member is in the first position, the first distal portion and the second distal portion are each bent radially outward from the central axis extending away from each other to define a mouth that has a larger opening than the open end of the channel, wherein the mouth is configured to receive a medicament delivery member shield between the first distal portion and the second distal portion, and wherein when the gripping member is moved to the second position, the first distal portion and the second distal portion are bent radially inward thereby closing the mouth around medicament delivery member shield such that the mouth opening is smaller than the open end of the channel.

14. The cap assembly of claim 12, wherein the gripping member further comprises:
a first flexible portion arranged between the first proximal portion and the first distal portion of the first leg; and a second flexible portion arranged between the second proximal portion and the second distal portion of the second leg.

15. The cap assembly of claim 14, wherein the inner cap structure has a first radial through-opening that receives the first flexible portion when the first flexible portion is in a first state and the gripping member is received by the channel, and wherein the inner cap structure has a second radial through-opening that receives the second flexible portion when the second flexible portion is in a first state and the gripping member is received by the channel.

16. The cap assembly of claim 14, wherein first distal portion and the second distal portion are each provided with a radially outwards extending protrusion configured to engage with a distal end of the inner cap structure to thereby prevent the first distal portion and the second distal portion from being received in the channel.

* * * * *